(12) United States Patent
Zhang

(10) Patent No.: US 9,499,890 B1
(45) Date of Patent: Nov. 22, 2016

(54) HIGH-STRENGTH, HIGH-TOUGHNESS STEEL ARTICLES FOR BALLISTIC AND CRYOGENIC APPLICATIONS, AND METHOD OF MAKING THEREOF

(71) Applicant: Xian Jie Zhang, Rockville, MD (US)

(72) Inventor: Xian Jie Zhang, Rockville, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 14/491,637

(22) Filed: Sep. 19, 2014

Related U.S. Application Data

(63) Continuation-in-part of application No. 13/443,413, filed on Apr. 10, 2012, now Pat. No. 8,899,904.

(60) Provisional application No. 61/888,752, filed on Oct. 9, 2013.

(51) Int. Cl.

| | |
|---|---|
| C21D 9/10 | (2006.01) |
| C22C 38/44 | (2006.01) |
| C22C 38/46 | (2006.01) |
| C22C 38/42 | (2006.01) |
| C22C 38/50 | (2006.01) |
| C21D 9/46 | (2006.01) |
| C21D 9/42 | (2006.01) |
| C21D 1/18 | (2006.01) |

(Continued)

(52) U.S. Cl.
CPC ............... *C22C 38/50* (2013.01); *C21D 1/18* (2013.01); *C21D 6/001* (2013.01); *C21D 6/004* (2013.01); *C21D 6/005* (2013.01); *C21D 6/008* (2013.01); *C21D 9/42* (2013.01); *C21D 9/46* (2013.01); *C22C 38/001* (2013.01); *C22C 38/02* (2013.01); *C22C 38/04* (2013.01); *C22C 38/06* (2013.01); *C22C 38/08* (2013.01); *C22C 38/12* (2013.01); *C22C 38/14* (2013.01); *C22C 38/16* (2013.01); *C22C 38/42* (2013.01); *C22C 38/44* (2013.01); *C22C 38/46* (2013.01); *C22C 38/48* (2013.01)

(58) Field of Classification Search
None
See application file for complete search history.

(56) References Cited

U.S. PATENT DOCUMENTS

| | | | |
|---|---|---|---|
| 4,634,462 A | 1/1987 | Fish et al. | |
| 4,814,141 A * | 3/1989 | Imai et al. | 420/109 |

(Continued)

FOREIGN PATENT DOCUMENTS

| | | | |
|---|---|---|---|
| EP | 1942203 A1 * | 7/2008 | |

OTHER PUBLICATIONS

U.S. Military Standard MIL-S-24645A (SH), Jan. 10, 1990.

(Continued)

*Primary Examiner* — Deborah Yee
(74) *Attorney, Agent, or Firm* — Howard Kaiser

(57) ABSTRACT

According to exemplary practice of the present invention, a steel composition includes, by weight, 0.07 to 0.15% C, 9 to 11% Ni, 0.8 to 1.2% Mo, 0.05 to 0.10% V, and further includes additives and/or impurities, with the balance being Fe. An iron alloy having such composition is produced and then undergoes heat treatment that includes quenching, lamellarization according to a 30 minute holding duration and a temperature span of 625° C. to 665° C., and tempering according to a 60 minute holding duration and a temperature span of 575° C. to 605° C. Exemplary embodiments of the inventive steel afford superior material properties including yield strength of at least 129 ksi, tensile strength of at least 157 ksi, elongation of at least 23%, and Charpy impact energy of at least 112 foot-pounds at −120° F.

12 Claims, 17 Drawing Sheets

(51) Int. Cl.
*C21D 6/00* (2006.01)
*C22C 38/48* (2006.01)
*C22C 38/16* (2006.01)
*C22C 38/14* (2006.01)
*C22C 38/12* (2006.01)
*C22C 38/08* (2006.01)
*C22C 38/06* (2006.01)
*C22C 38/04* (2006.01)
*C22C 38/02* (2006.01)
*C22C 38/00* (2006.01)

(56) References Cited

U.S. PATENT DOCUMENTS

| | | | |
|---|---|---|---|
| 5,122,336 A | 6/1992 | Roux et al. | |
| 5,482,675 A | 1/1996 | Shotwell et al. | |
| 5,651,938 A | 7/1997 | Thomson et al. | |
| 5,827,379 A * | 10/1998 | Okamura et al. | 148/621 |
| 7,981,521 B2 | 7/2011 | Bailey et al. | |
| 8,092,620 B2 | 1/2012 | Sadhukhan et al. | |
| 8,308,873 B2 | 11/2012 | Chin et al. | |
| 8,518,195 B2 | 8/2013 | Bradley | |
| 8,580,051 B2 | 11/2013 | Chin et al. | |
| 8,641,836 B2 | 2/2014 | Ishikawa et al. | |
| 8,715,427 B2 | 5/2014 | Vandeputte et al. | |
| 8,899,094 B1 | 12/2014 | Zhang | |
| 9,121,088 B2 | 9/2015 | Bailey et al. | |
| 2012/0144989 A1 | 6/2012 | Du Plessis et al. | |
| 2012/0174749 A1 | 7/2012 | Stumpf et al. | |
| 2013/0037176 A1 | 2/2013 | Novotny | |
| 2013/0146182 A1 | 6/2013 | Novotny | |
| 2014/0116578 A1 | 5/2014 | Zhang et al. | |

OTHER PUBLICATIONS

U.S. Military Standard MIL-DTL-12560J (MR), Jul. 24, 2009.
U.S. Military Standard MIL-DTL-12560K (MR), Dec. 7, 2013.

* cited by examiner

FIG. 3 — Signature Microstructure

SEI image

Ni map

Fe map

Ni (lighter areas) and Fe (darker areas) map

HIGH-STRENGTH, HIGH-TOUGHNESS STEEL ARTICLES FOR BALLISTIC AND CRYOGENIC APPLICATIONS, AND METHOD OF MAKING THEREOF

CROSS-REFERENCE TO RELATED APPLICATIONS

This application is a continuation-in-part of U.S. nonprovisional application Ser. No. 13/443,413 now U.S. Pat. No. 8,889,094, incorporated herein by reference, filing date 10 Apr. 2012, title "Evaluation of Ballistic Resistance of Steel in Terms of Ballistically Induced Plasticity," inventor Xian Jie Zhang.

This application claims the benefit of U.S. provisional application Ser. No. 61/888,752, incorporated herein by reference, filing date 9 Oct. 2013, title "High-Strength, High-Toughness Steel Compositions and Articles for Ballistic and Cryogenic Applications," inventor Xian Jie Zhang.

BACKGROUND OF THE INVENTION

The present invention relates to steel, more particularly to steel compositions and articles that are characterized by high-strength and high-toughness and that are suitable for ballistic or cryogenic use.

Steel is an alloy that contains iron and carbon. Steel is often used as a structural material, and has been known in a variety of formulations; generally speaking, steel properties will vary in accordance with steel formulations. Steel typically contains predominately iron, about 0.2% to 1.5% carbon (weight percent), and at least one other constituent such as aluminum, chromium, cobalt, copper, manganese, molybdenum, nickel, phosphorus, silicon, sulfur, or tungsten. Desirable properties of steel may include strength, toughness, durability, malleability, hardness, ductility, ballistic resistance, cryogenic efficacy, etc.

The following references, each of which is incorporated herein by reference, are informative on ballistic and other properties of steel: T. BØrvik, S. Dey and A. H. Clausen: *Int. J. Impact Eng.*, 2009, 36, 948-964; J. F. Chinella and M. G. H. Wells: ARL-RP-64, US, February 2003; S. N. Dikshit, V. V. Kutumbarao and G. Sundararjan: *Int. J. Impact Eng.*, 1995, 16, 293-320; W. Gooch, M. Burkins and D. Mackenzie: 22nd Int. Symposium on Ballistics, Vancouver, Canada, 2005; S. J. Manganello and K. H. Abbott: J. of Materials, 1972, 231-239; D. D. Showalter, W. A. Gooch, M. S. Burkins, J. S. Montgomery and R. Squillacioti: *AMMTIAC*, 2010, Vol. 4, No. 4, 2010; D. D. Showalter, W. A. Gooch, M. S. Burkins and R. Stockman Koch: ARL-TR-4632, US, 2008; D. D. Showalter, W. A. Gooch, M. S. Burkins, V. Thorn, S. Cimpoeru and R. Barnett: ARL-RP-181, US, 2007; D. D. Showalter, W. A. Gooch, M. Burskins, J. Montgomery and R. Squillacioti: ARL-TR-4997, 2009.

SUMMARY OF THE INVENTION

An object of the present invention is to provide a high-strength, high-toughness, low-carbon Ni steel that exhibits superior properties such as ballistic resistance and cryogenic robustness. A further object of the present invention is to provide such a steel alloy that is suitable for many naval applications.

Exemplary practice of the present invention provides a steel material or steel product (e.g., a steel plate) that includes: 0.07 to 0.15% C by weight; 9 to 11% Ni by weight; 0.8 to 1.2% Mo by weight; 0.05 to 0.10% V by weight; additives and/or impurities. The balance of the inventive steel is Fe. To make the inventive steel, an iron alloy is formed and is then heat-treated according to a QLT process that includes the following: (i) quenching characterized by a one hour holding time and a temperature span of 780° C. to 820° C.; (ii) lamellarizing characterized by a 30 minute holding time and a temperature span of 625° C. to 655° C. or a temperature span of 635° C. to 665° C.; (iii) tempering characterized by a one hour holding time and a temperature span of 575° C. to 605° C. Superior properties of the present invention's steel may include one, some, or all of the following: (i) yield strength of at least 129 ksi; (ii) tensile strength of at least 157 ksi; (iii) elongation of at least 23%; (iv) Charpy impact energy of at least 112 foot-pounds at $-120°$ F.

The present invention represents a high strength, high toughness, and superior FSP ballistic resistance steel having excellent cryogenic properties. Exemplary embodiments of the inventive steel composition include, in weight: 0.07 to 0.15% C; 9 to 11% Ni; 0.8 to 1.2% Mo; and, 0.05 to 0.10% V. The inventive steel composition also includes additives and/or impurities, with the balance being Fe. The additives/impurities may include one, some, or all of the following: 0.5 to 0.7% Mn; 0.5 to 0.7% Cr; 0.15 to 0.25% Si; 0.1 to 0.2% Cu; 0.001 to 0.010% Nb; 0.02 to 0.05% Al; 0.001 to 0.010% Ti; 0.001 to 0.005% Ca; not more than 0.009% N; not more than 0.003% O; not more than 0.009% P; and not more than 0.004% S. Mn, Cr, Si, Cu, Nb, Al, Ti, and Ca may manifest as additives. N, O, P, and S may manifest as impurities.

Exemplary inventive embodiments are new steels that exceed the ballistic resistance, strength, and toughness of current naval ship steel plates. In his testing, the present inventor's optimally QLT (quench-lamellarize-temper) treated low-carbon 10% Ni steel plates displayed exceptional properties in all of these aspects, when compared to the widely-used HSLA-100 steel plates. The inventive steel plates demonstrated superior toughness, improvement of over 15% in strength, and improvement of over 15% in 20 mm FSP ballistic limit $V_{50}$.

In inventing his novel 10Ni steel, the present inventor sought to determine chemical compositions and QLT (quench-lamellarize-temper) ranges of his steel that consistently exhibit superior properties and are compatible with commercial production. The present inventor's approach to inventing his steel involved three phases. First, he determined, by high-speed dilatometric tests and metallography, an effective QLT (quench-lamellarize-temper) process matrix for five 10Ni steel heats with a carbon range from 0.07% to 0.15%. Second, he conducted .30 caliber FSP (fragment simulation projectile) ballistic resistance $V_{50}$ and mechanical property evaluation of thirty-nine test plates of the five 10Ni steel heats heat-treated with the QLT process matrix. Third, he performed extensive post-test characterization and analysis.

The present invention, as frequently embodied, is a low carbon 10Ni steel having attributes of high strength, high toughness, and superior ballistic resistance. The inventive 10Ni steel is superior to naval steel HSLA-115 ("HSLA" is an acronym for "High-Strength, Low-Alloy"), currently used by the U.S. Navy, and could further improve the performance and survivability of the U.S. Naval Fleet. A portable technology is nearly ready for commercial production of inventive steel formulations and products.

Testing of steel plates that were made of the present invention's optimally QLT-treated 10Ni steel demonstrated its superiority in terms of properties including strength, toughness, and ballistic resistance. For instance, inventive QLT 10 Ni steel was characterized by a yield strength of approximately 130 ksi; in contrast, HSLA-100 was characterized by a yield strength of 100 ksi. Note the estimated yield strength of RHA Class 2 steel armor in the range 90 to 125 ksi. Furthermore, inventive QLT 10 Ni steel was characterized by a Charpy energy, at −120° F., of approximately 113; in contrast, HSLA-100 steel was characterized by a Charpy energy, at −120° F., of 100. Note that RHA Class 2 steel armor is reported to have a Charpy energy, at −40° F., in the range 35 to 55. Moreover, inventive QLT 10 Ni steel was characterized by a 20 mm FSB ballistic limit ($V_{50B}$) of approximately 115%, based on normalization, as 100%, of the 20 mm FSB ballistic limit for HSLA-100 steel. Based on this 100% normalization for HSLA-100, RHA Class 2 armor was characterized by a 20 mm FSB ballistic limit ($V_{50B}$) of ≥95%.

Incorporated herein by reference is a 23-page slide presentation presented by the present inventor, as follows: Xian Jie Zhang, Naval Surface Warfare Center, Carderock Division (NSWCCD), "The Effect of Ballistic-Induced Plasticity (BIP) on the Ballistic Performance of QLT Treated Low-Carbon 10 Ni Steel," Materials Science and Technology Conference (MS&T 2012), Pittsburgh, Pa., 7-11 Oct. 2012, presented on 10 Oct. 2012. This presentation is included in the aforementioned U.S. provisional application Ser. No. 61/888,752.

Also incorporated herein by reference is a 14-page paper co-authored by the present inventor, as follows: Dieter Isheim, Allen H. Hunter, Xian Jie Zhang, and David N. Seidman, "Nanoscale Analyses of High-Nickel Concentration Martensitic High-Strength Steels," Metallurgical and Materials Transactions A, The Minerals, Metals & Materials Society and ASM International 2013, Volume 44A, July 2013, pages 3046-3059. This paper is included in the aforementioned U.S. provisional application Ser. No. 61/888,752.

BRIEF DESCRIPTION OF THE DRAWINGS

The present invention will now be described, by way of example, with reference to the accompanying drawings, wherein:

FIGS. 4 through 7 illustrate superiority, to the other steels, of each of the optimally QLT treated 10 Ni steels in accordance with the present invention.

FIG. 15 is a map showing nickel, FIG. 16 is a map showing ferrite, and FIG. 17 is a map showing both nickel and ferrite.

DESCRIPTION OF EXEMPLARY EMBODIMENTS OF THE INVENTION

Figure 1:
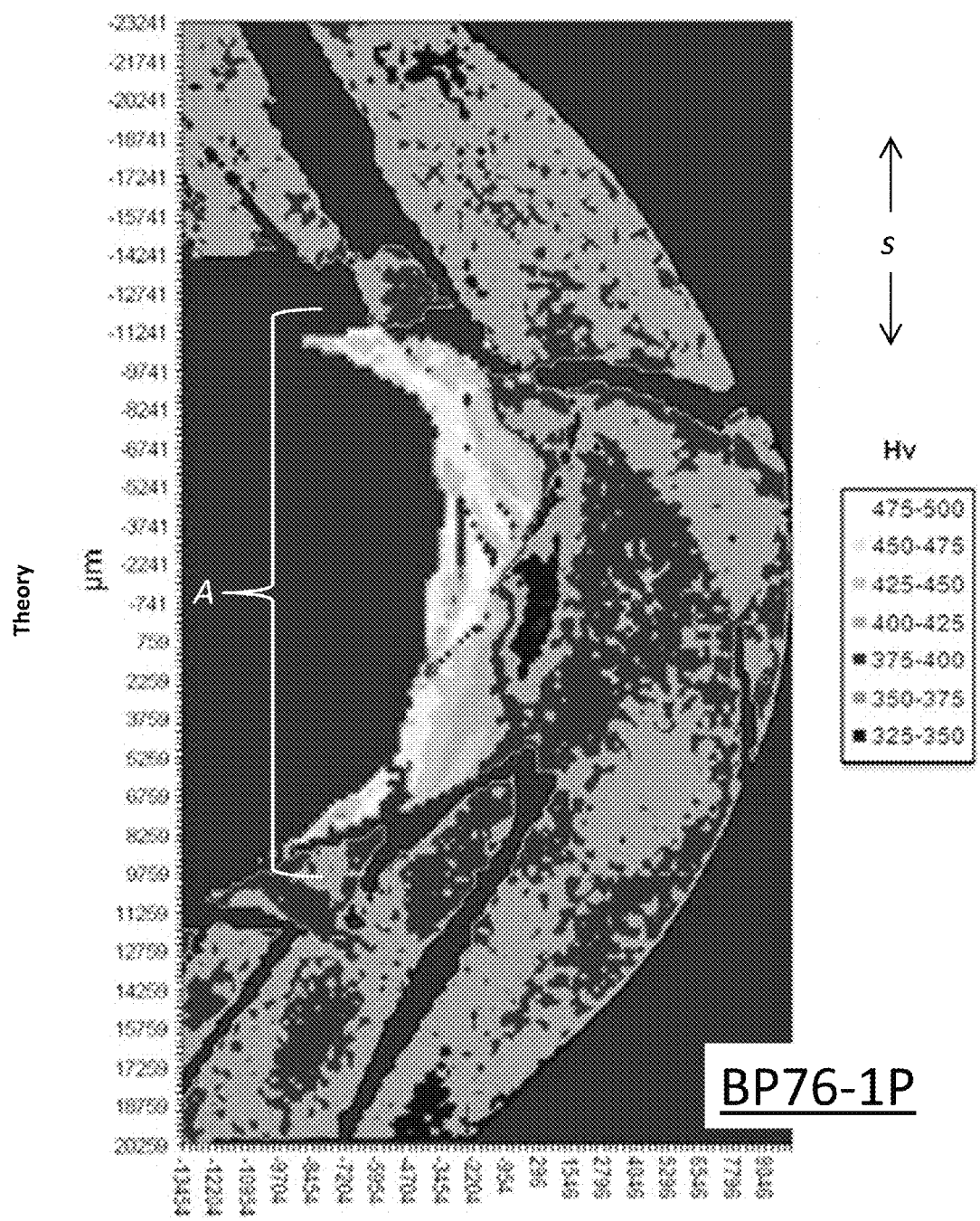
FIG. 1 is a graphically contextualized photographic image conveying a microhardness map of sectioned crater BP76-1P of 10 Ni steel, in accordance with the present invention.
Figure 2:
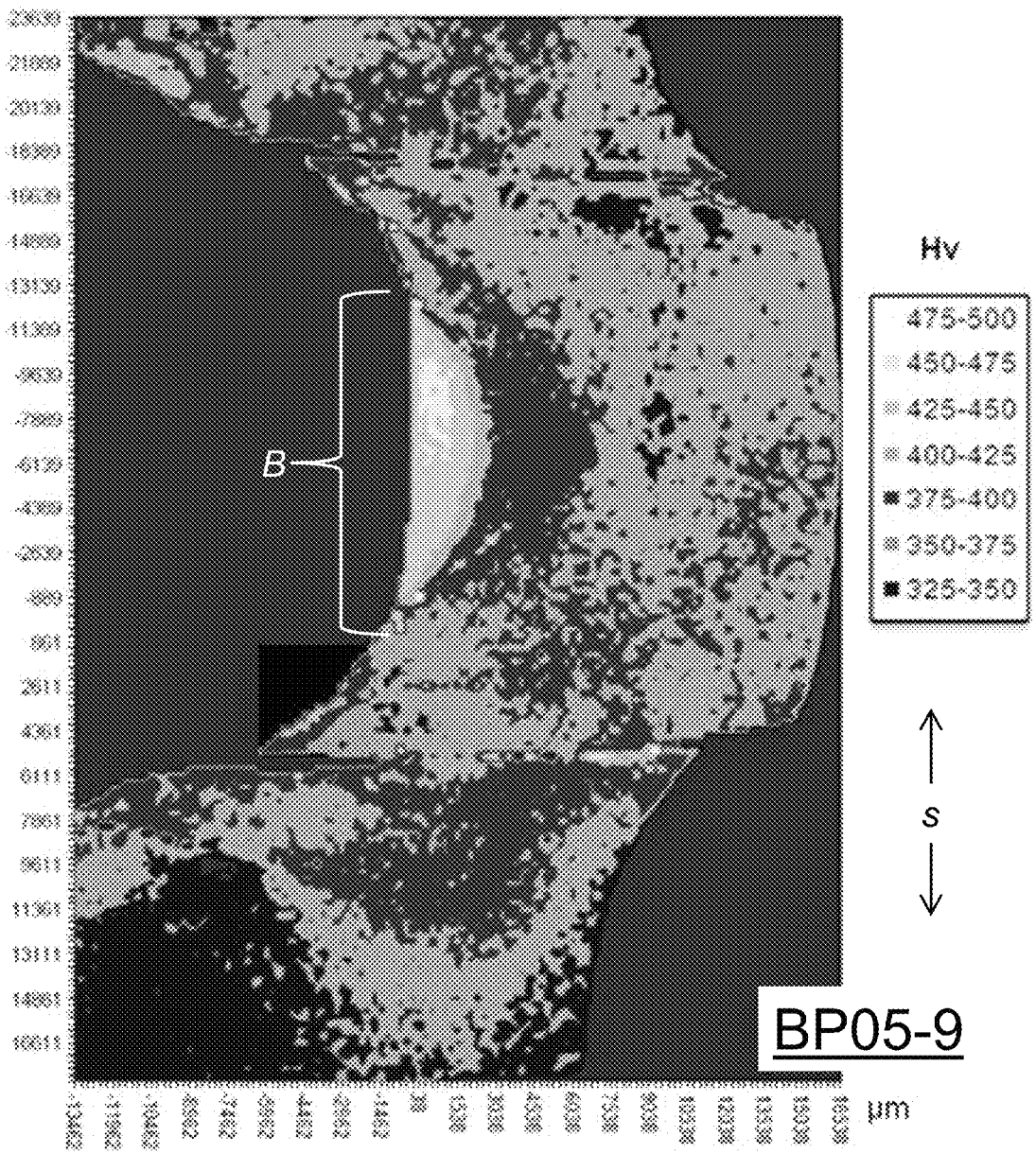
FIG. 2 is a graphically contextualized photographic image conveying a microhardness map of sectioned crater BP05-9 of 10 Ni steel, in accordance with the present invention.

Reference is now made to FIGS. 1 and 2, which are also presented and discussed in the present inventor's aforesaid parent application, viz., U.S. nonprovisional application Ser. No. 13/443,413, filed 10 Apr. 2012, entitled "Evaluation of Ballistic Resistance of Steel in Terms of Ballistically Induced Plasticity." The present inventor measured the spatial microhardness distribution of deformed targets by mapping microhardness measurements onto transverse sections of ballistic craters.

FIGS. 1 and 2 are grayscale versions of color microhardness maps obtained by the present inventor. In each figure, seven Vickers hardness (HV) number ranges are shown, viz., 475-500 HV, 450-475 HV, 425-450 HV, 400-425 HV, 375-400 HV, 350-375 HV, and 325-350 HV. The higher a Vickers hardness number, the harder the material. The hardness distribution maps shown in FIGS. 1 and 2 are plotted on the same scale, allowing for intuitive dimensional comparisons. High-hardness region A (shown in FIG. 1) and high-hardness region B (shown in FIG. 2) are the microhardness-map regions that are characterized by the highest hardness ranges, viz., primarily ranging between 425 HV and 500 HV, in their respective microhardness maps.

To map the microhardness measurements, the present inventor used Clemex CMT Lite, a software product manufactured by Clemex Technologies Inc., 800 Guimond, Longueuil, Quebec, J4G 1T5, Canada. One crater from each of two ballistic plates was selected for the mapping. Crater BP76-1 P was cut from ballistic plate BP76, which was optimally QLT-treated and exhibited a ballistic limit of 118% $V_{50B}$. Crater BP05-9 was cut from ballistic plates BP05, which were QL-treated with a ballistic limit of 89% $V_{50B}$.

The present inventor found that the 33% higher 20 mm FSP ballistic resistance of BP76 relative to that of BP05 was due solely to differences in their respective heat-treatments (Both samples were low-carbon 10% (weight percent) Ni steels with nearly identical chemical composition). The crater for each plate was created by a projectile at its respective $V_{50}$ speed, meaning the striking speed of the projectile for crater BP76-1P was 33% higher than that of crater BP05-9. Microhardness measurements were made 250 μm apart with a load of 300 gf. Results were binned in 25 Hv increments indicated in the key shown in each of FIG. 1 and FIG. 2.

Notable visual comparisons can be drawn between high-hardness region A and high-hardness region B, as revealed in the cross-sectional images of FIGS. 1 and 2. High-hardness region A generally describes an arcuate shape.

High-hardness region B generally describes a circular segment shape. High-hardness region A has a greater geometric two-dimensional area than has high-hardness region B. Similarly shown in FIGS. 1 and 2, the plate's ballistic crater generally extends diametrically in transverse direction s, which is approximately perpendicular to the ballistic direction of the projectile. High-hardness region A is more extensive (e.g., longer) than high-hardness region B in transverse direction s. High-hardness region A extends further than high-hardness region B, in transverse direction s, both above and below the immediate strike (impact) area.

Figure 14:
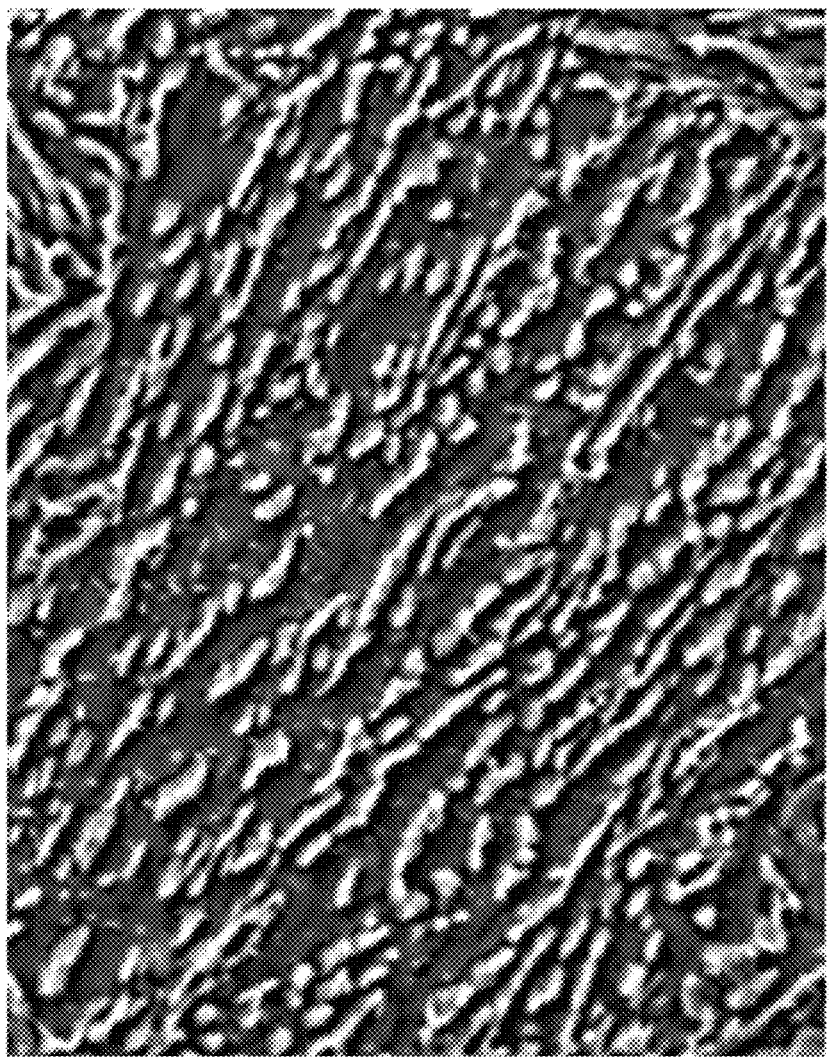
FIG. 14 is a secondary electron image (SEI) of ballistic test plate A5, made in accordance with the present invention. The SEI was obtained using a scanning electron microscope (SEM).
Figure 15:
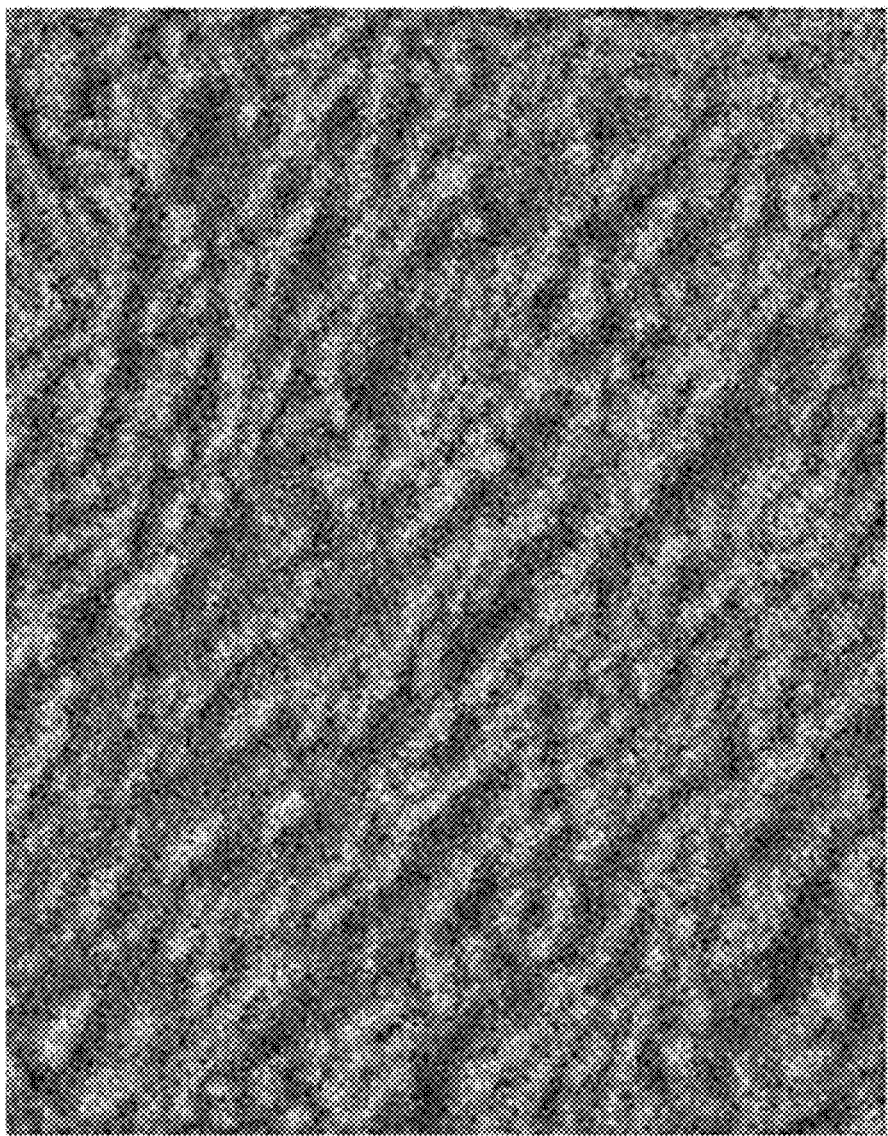
FIGS. 15 through 17 are energy-dispersive X-ray spectrometry (EDS) images of the ballistic test plate shown in FIG. 14.
Figure 16:
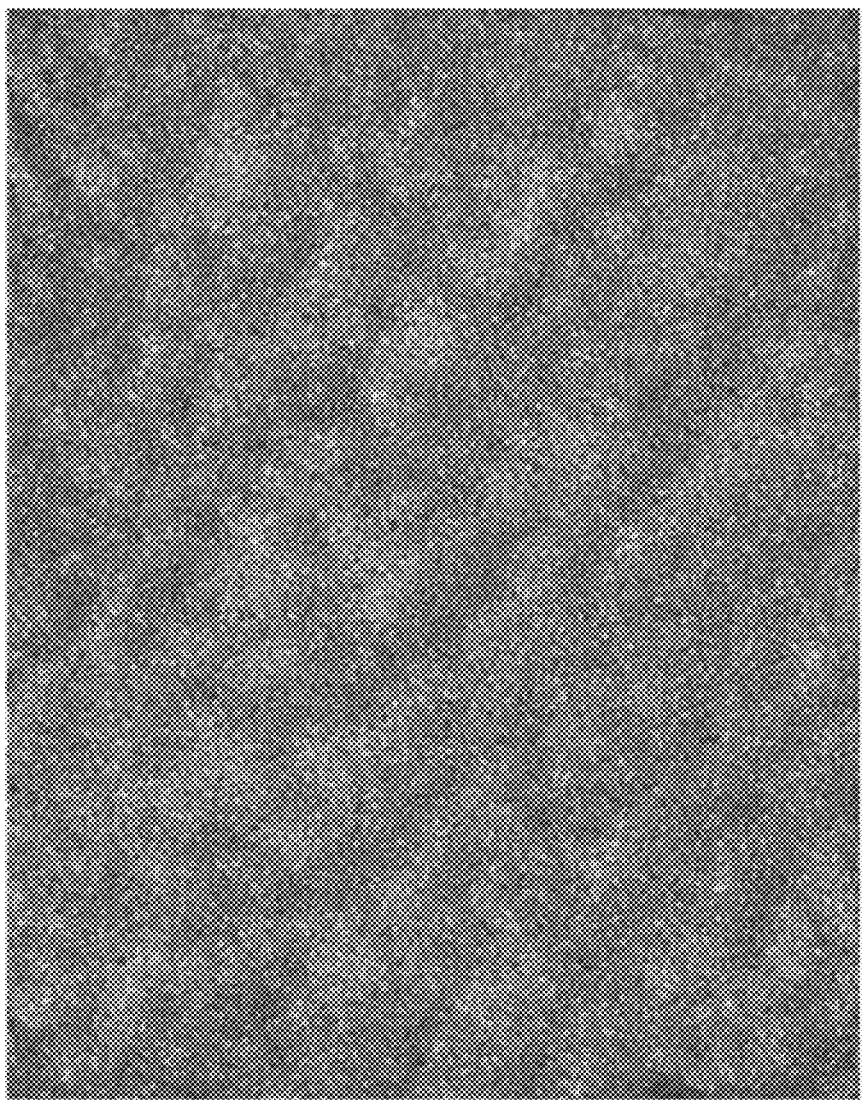
Figure 17:
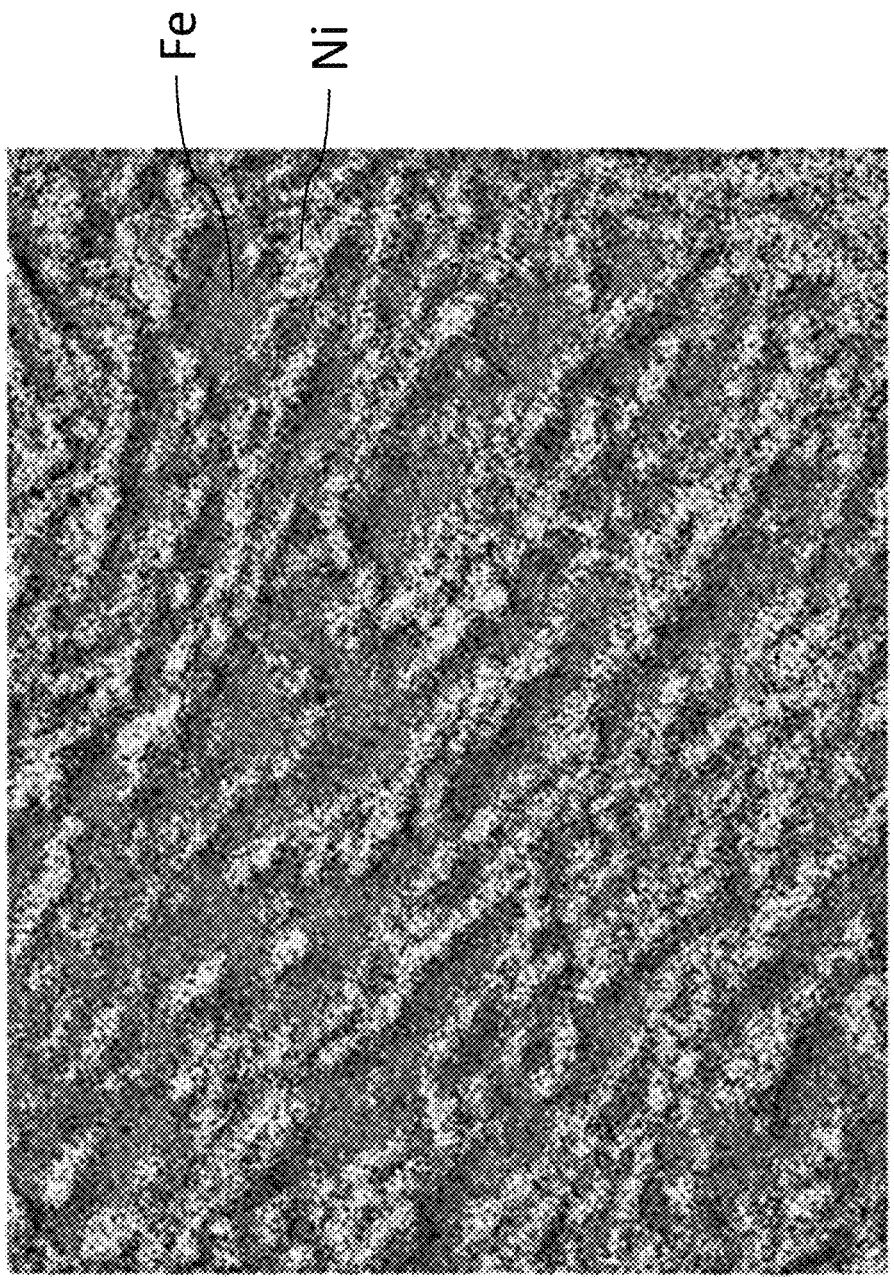

FIG. 14 of the aforesaid U.S. application Ser. No. 13/443,413 summarizes pertinent information about these two craters before and after ballistic testing. It should be noted that these two plates had identical initial hardness. Important ballistic perforation characteristics of craters BP76-1P and BP05-9 were observed. Using the global thickness reduction, 1-tm/ti, as a simple indicator of the total amount of global dynamic deformation, crater BP76-1 P underwent significantly more global deformation than crater BP05-9. In other words, crater BP76-1P absorbed far more kinetic energy of the striking projectile via global deformation than crater BP05-9.

Each hardness distribution map (FIGS. 1 and 2) directly reflects the degree of strengthening and its spread in the crater. The strengthening can occur through either martensite phase transformation strengthening or dynamic strain hardening. Both mechanisms occur during the ballistic perforation process of a crater with substantial austenite content. As the two hardness distribution maps clearly indicate, the strengthening was significantly greater and spread over a larger area in crater BP76-1 P (FIG. 1) than in crater BP05-9 (FIG. 2).

The microhardness map findings were consistent with VSM measurements, which showed that almost all of the austenite precipitates (19% volume fraction) in the QLT treated crater BP76-1 P transformed into martensite during the ballistic testing. The martensite transformation enhanced the dynamic plasticity and strengthening effect, thus absorbing more kinetic energy, resulting in higher ballistic limit $V_{50}$ of BP76. In comparison, based on magnetometer measurements of similar samples, the BP05 austenite volume fraction was only 5-8%. This was likely the key reason that the BP05 exhibited lower ballistic limit $V_{50}$.

The hardness map of crater BP09-5 showed local adiabatic shear bands (ASBs) that caused a plugging failure. More importantly, because strengthening surrounding the ASBs was moderate and localized, it is evident that this type of process could not dissipate a substantial amount of energy, and resulted in a lower ballistic resistance for BP05. In comparison, there was no indication of the formation of ASB in crater BP76-1P, and the projectile was stopped by extensive plastic bulging of the strengthened target as it absorbed more energy.

The microhardness maps were also informative of the deformation and failure sequence of the ballistic perforation process. Generally speaking, dynamic global deformation must occur prior to local adiabatic sheer banding (ASB) formation. The more dissipated the target deformation is, the less likely ASB is to occur. If the target deforms and strengthens spontaneously upon a strike, the deformation spreads quickly and widely, absorbing much of the energy of the projectile.

As depicted in FIG. 1, because there was less projectile potential energy remaining to cause ASB, the target bulged instead of forming a plug, resulting in a significantly higher ballistic resistance $V_{50}$. The austenite precipitate content in BP76 was sufficient to allow the ballistic-induced austenite-to-martensite transformation to occur. This phenomenon, discovered by the present inventor and dubbed "Ballistically Induced Plasticity" (acronym, "BIP") by him, was the key to the improvement of the ballistic behavior of the optimally QLT-treated low-carbon 10% Ni steel. Ballistically induced plasticity was intuitively revealed to the present inventor by the microhardness maps.

Figure 3:
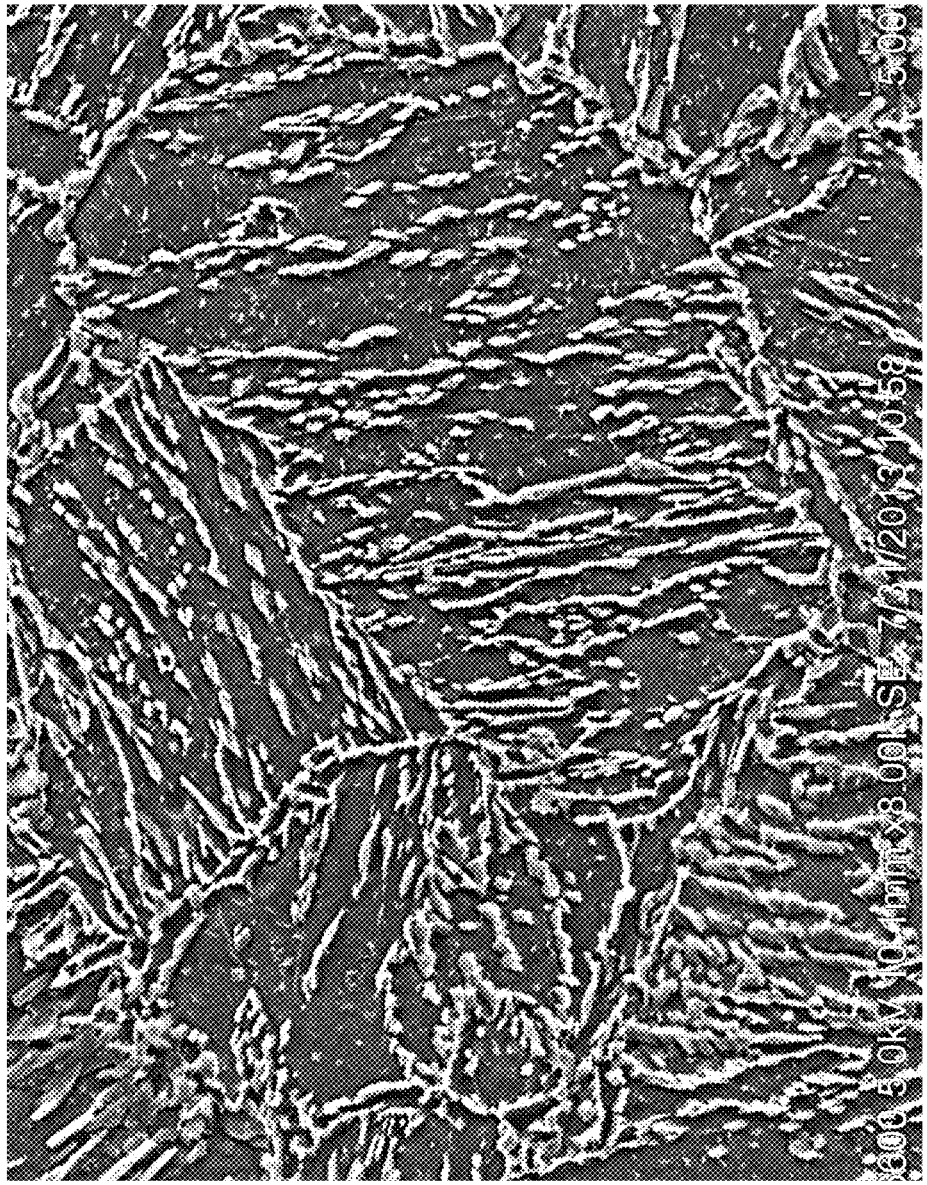
FIG. 3 is a photographic image of an optimal QLT treated 10 Ni ballistic sample, characterized by fine austenite precipitates in a ferrite matrix.

From metallographic observations, it was clear to the present inventor that the austenite precipitates were controlling ballistic performance. FIG. 3 shows the microstructure of a low-carbon 10% Ni steel ballistic sample treated with an optimal QLT process in accordance with the present invention. The microstructural depiction of FIG. 3 may be described as "signature" to many steels in accordance with the present invention. In testing conducted by the present inventor, this sample was compared with two other samples, viz., a low-carbon 10% Ni steel ballistic sample treated with a QT process, and a low-carbon 10% Ni steel ballistic sample treated with a QL process. Among the three steel samples tested, differences were manifest in the amount, size, shape, and distribution of austenite precipitates. These differences correlated with significant differences in ballistic limit $V_{50}$.

The QT-treated sample had microstructure consisting of tempered lath martensite, and exhibited a low 20 mm FSP ballistic limit of 82% $V_{50B}$. The QL sample showed long rods consisting of mixtures of martensite and austenite (M+A), which indicated that austenite rods first formed during the intercritical heating (L-process) and then partially transformed to martensite in subsequent cooling, and improving ballistic limit to 99% $V_{50B}$. In the optimally QLT-treated sample (FIG. 3), the long (M+A) rods that formed at the first intercritical heating process (L-process) further decomposed into finer austenite particles and a ferrite matrix in the second intercritical heating process (T-process), resulting in a superior ballistic limit of 118% $V_{50B}$. These findings by the present inventor are unique insofar as they directly and quantitatively correlate the amount and morphology of a single microconstituent, the austenite precipitates, with the FSP ballistic limit of steel targets.

Figure 4:
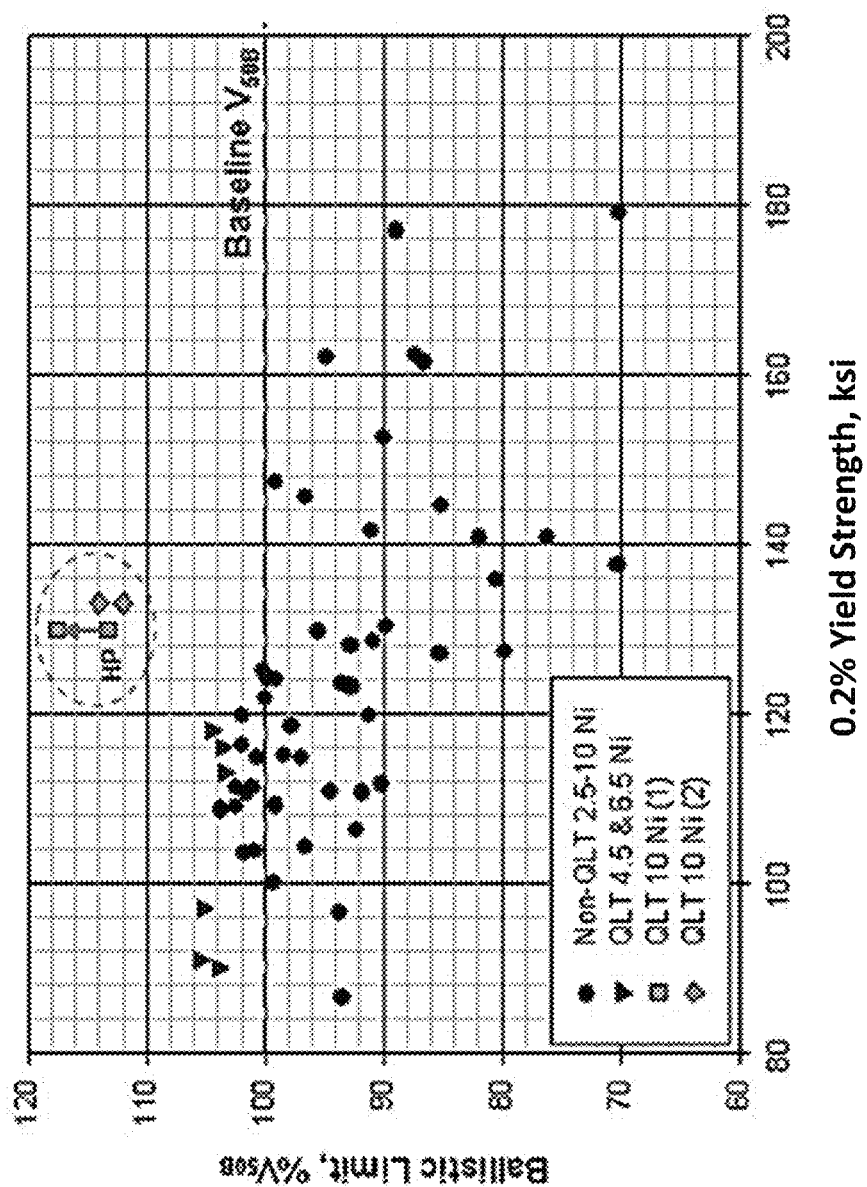
FIGS. 4 through 7 are graphs comparing performances among various steels with respect to various mechanical properties. Each plot displays 20 mm FSP ballistic limit $V_{50}$ (y-axis) versus a mechanical property (x-axis), and compares performances, with respect to a particular mechanical property, among two different optimally QLT treated 10 Ni steels and various other steels.
Figure 5:
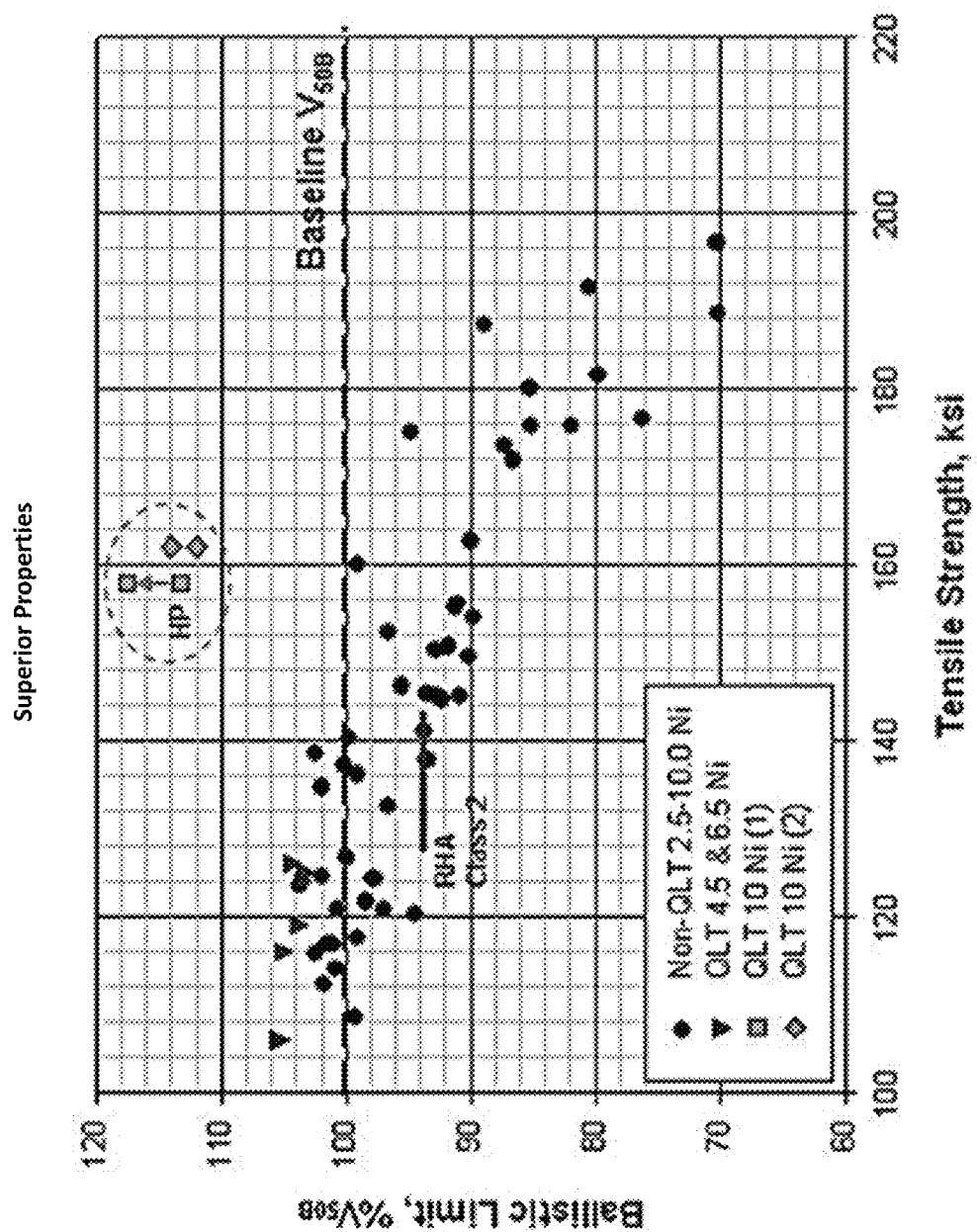
Figure 6:
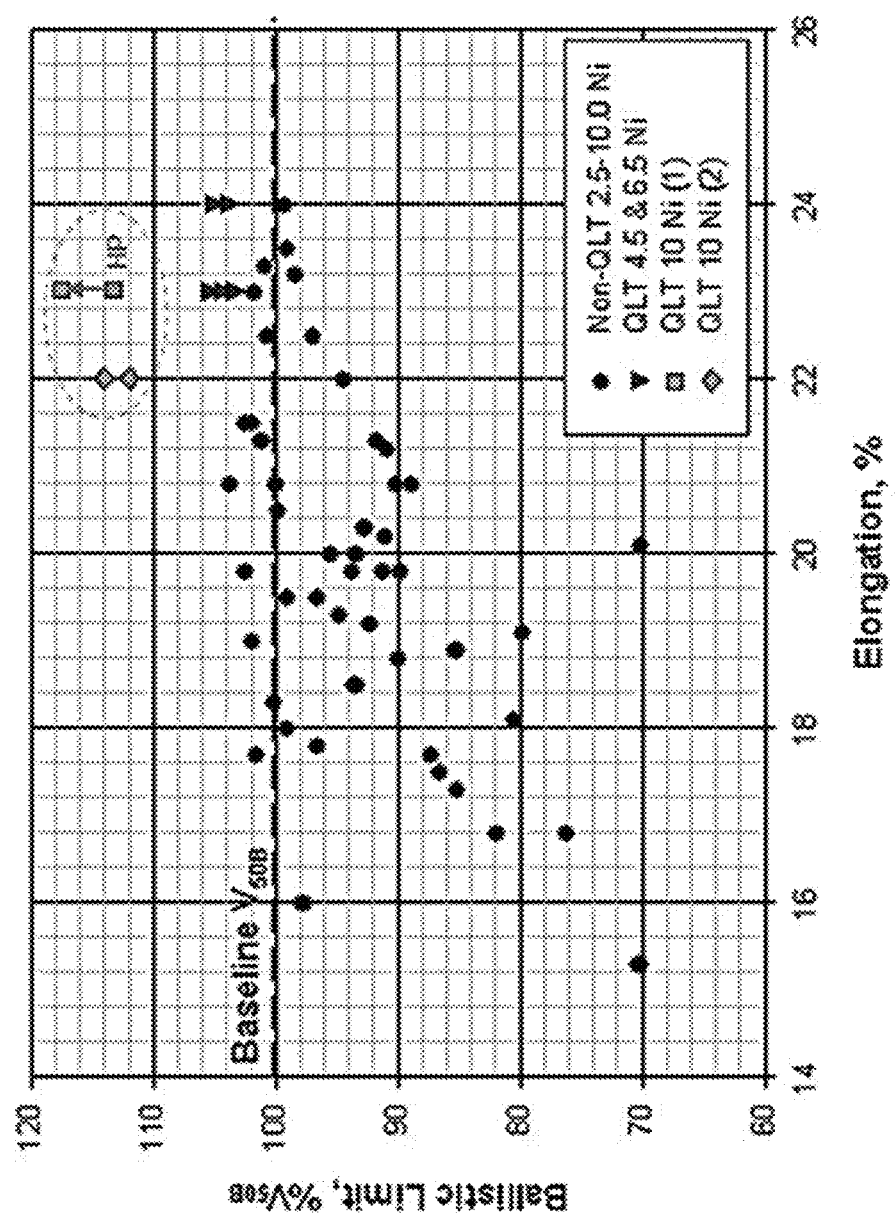
Figure 7:
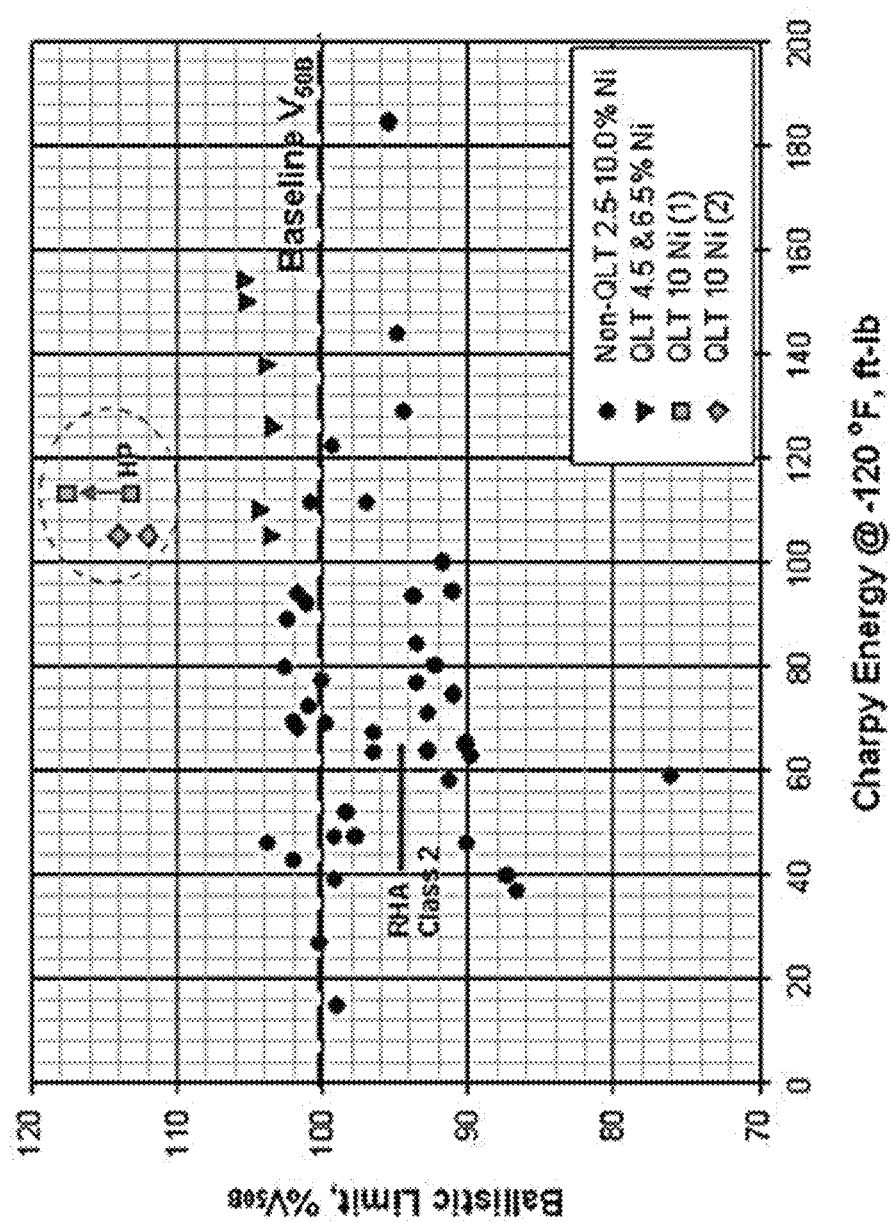

With reference to FIGS. 4 through 7, the testing conducted by the present inventor demonstrated breakthrough results. Optimal QLT-processed 0.09% C-10% Ni steel plates (heats H007 and H008) were shown by the present inventor to possess overall properties superior to the widely used HSLA-100 steel plates (such as produced according to U.S. Military Standard MIL-S-24645A (SH)), as well as superior to plates of the same 10Ni steel heat treated by other processes. FIGS. 4 through 7 illustrate superior overall properties (FIG. 4, yield strength; FIG. 5, tensile strength; FIG. 6, elongation; FIG. 7, Charpy energy) of the present inventor's optimally QLT processed 0.09C-10Ni steel plates. The present inventor's test results were consistent with his novel theory of BIP (ballistically induced plasticity) as the underlying mechanism that results in increased strength, toughness, and fragment-simulating projectile (FSP) ballistic resistance in his new steel.

The "ballistic limit $V_{50}$" may be defined as the average velocity of an equal number of the highest partial penetration velocities and the lowest complete penetration velocities that occur within a specific velocity spread. "$V_{50}$" (or "V-50," or "V50") symbolizes "velocity-fifty-percent." In the data presented in FIGS. 4 through 7, the measured ballistic limit $V_{50}$ was normalized to the ballistic limit of a baseline HSLA-100 (2.5% Ni) steel sample, and termed the "$V_{50B}$." Tensile properties and low-temperature (−120° F.)

impact toughness data were measured either on small pieces cut from the tested ballistic plates, or small coupons heat-treated with the ballistic plates.

The test results are summarized in FIGS. 4 through 7, which graphically convey ballistic limit $V_{50}$ results (y-axis) versus mechanical properties (x-axis). The present invention's optimally QLT treated 10% Ni steel outperformed all other steel plates, displaying a substantially higher ballistic limit $V_{50}$ at a substantially higher strength level, and contradicting a commonly observed reverse-correlation in steel in general between FSP ballistic limit and strength. The inventive steel plates displayed exceptional overall properties, including an improvement of more than 15% in both 20 mm FSP ballistic limit $V_{50}$ and strength (e.g., yield strength), as well as superior toughness, when compared to the widely used HSLA-100 steel plates.

The 20 mm ballistic limit of an embodiment the inventive steel is shown in FIGS. 4 through 7 to be at least 113% of the $V_{50B}$; that is, the 20 mm ballistic limit of the inventive steel is at least 13% higher than the 20 mm ballistic limit of HSLA-100. An embodiment of an inventive steel plate is shown in FIG. 7 to have a Charpy impact energy that is at least 71% higher than that of RHA (rolled homogeneous armor, such as produced according to U.S. Military Standard MIL-DTL-12560J (MR)). FIG. 4 illustrates a 0.2% yield strength of the inventive steel of at least 129 ksi, in conjunction with a ballistic limit of at least 113% $V_{50B}$. FIG. 5 illustrates a tensile strength of the inventive steel of at least 157 ksi, in conjunction with a ballistic limit of at least 113% $V_{50B}$. FIG. 6 illustrates an elongation of the inventive steel of at least 23%, in conjunction with a ballistic limit of at least 113% $V_{50B}$. FIG. 7 illustrates a Charpy impact energy of the inventive steel of at least 112 foot-pounds at minus 120 degrees Fahrenheit, in conjunction with a ballistic limit of at least 113% $V_{50B}$.

One of present inventor's goals was to determine the chemical composition and QLT-process range that not only enable the steel to consistently exhibit the demonstrated superior properties, but also are compatible with commercial production. This goal has been fundamentally achieved through three phases, as elaborated upon hereinbelow.

In the first phase, the present inventor determined an effective QLT process matrix for five VIM 10Ni steel heats with a carbon range between 0.07% and 0.15% (weight percent). He did this via a comprehensive high-speed Gleeble dilatometric study on the phase transformation characteristics of the QLT processes of these 10 Ni steels. He used this matrix to heat-treat thirty-nine ballistic test pieces of the steel heats.

In the second phase, the present inventor conducted a series of .30 caliber FSP (fragment-simulation-projectile) ballistic resistance $V_{50}$ tests on the aforementioned thirty-nine 0.25" thick plates of the five 10% Ni steel heats. Basically, "$V_{50}$" can be defined as the velocity at which 50% of the projectiles impacting an armor system at its frontal side will be stopped by the armor system. "$V_{50}$" (or "V-50," or "V50") symbolizes "velocity-fifty-percent." The results of the ballistic resistance $V_{50}$ testing were satisfactory, indicating that the $V_{50}$ values (after thickness correction) of these thirty-nine samples were clustered within a narrow band that deviated no more than 4% from a reference value $V_{50R}$. This reference value was the ballistic resistance of a sample from the same steel heat (H007) and heat treated with the same QLT process as the samples that showed superior properties in FY11 tests. Considering the nature of the ballistic resistance $V_{50}$ test, this ±4% scatter is acceptable for commercial product and engineering ballistic applications.

In the third phase, the present inventor measured mechanical properties of the thirty-nine tested ballistic plates—two 0.25" flat tensile samples and three sub-sized Charpy V-notch impact specimens from each plate—for a total of seventy-eight tensile specimens and one hundred seventeen Charpy impact specimens. The strength and impact toughness of QLT-processed 10 Ni steel plates was found to be a function of their carbon content, while the FSP ballistic resistances of all samples fell within a narrow range. This unique combination of ballistic resistance and mechanical properties suggests an opportunity to produce a range of commercial 10Ni steel products that possess a superior FSP ballistic resistance coupled with a range of mechanical properties, because current commercial steelmaking technology can control the carbon content within a very tight range, e.g., about 0.02.

In sum, the U.S. Navy's FY13 goal of determining the optimal chemical composition and QLT process range for the 10Ni steel was achieved by the present inventor. Further, a portable technology is nearly ready for commercial production, only perhaps pending further confirmatory tests with different steel heat sizes, plate thickness, and ballistic projectile calibers.

Additionally, the present inventor explored other possible applications of his QLT 10 Ni steel. In a proprietary context, a major steel company recognized that the inventive 10Ni steel far exceeds the current cryogenic steel SA553 requirements, despite being 60 percent stronger. The major company suggested the possibility that the inventive 10Ni steel could be adapted and refined to be used as a new, ultra-high-strength, plate steel for energy-related commercial cryogenic applications. A joint effort by the U.S. Navy and the company is proceeding toward this goal.

The present inventor obtained key results in areas including the following: (i) production of 0.25 inch plates of five VIM 10% Ni steel heats with a carbon content range between 0.07% and 0.15%; (ii) determination of an optimal QLT process matrix through a comprehensive high-speed Gleeble dilatometric study on a large number of 10NI steel heat H007 samples; (iii) performance of caliber .30 FSP ballistic tests of QLT-processed 0.07-0.15% C and 10% Ni steel plates.

In consideration of the availabilities of the steel mill and hot-rolling facility, a smaller ballistic threat (.30 Cal. FSP) and a thinner plate (0.25 inch) were selected by the present inventor for this study, instead of 20 mm FSP and 1-inch plate that he used in previous tests. One-inch and thicker plates from previous four 400 lb VIM 10Ni steel heats and 100 lb ingots from two new 100 lb VIM heats were hot-rolled into 0.25-inch plates. Fifty-nine 0.25-inch ballistic test pieces were made in total, of which thirty-nine pieces were tested.

Table 1, below, summarizes the nominal chemical composition and test samples of the five steel heats. In addition to iron (Fe) and the elements indicated in Table 1, all heats have the following nominal content (weight percent): 0.60% chromium (Cr); 0.60% manganese (Mn); 0.20% silicon (Si); 0.15% copper (Cu); 0.03% aluminum (Al); 0.02% titanium (Ti); 0.002% calcium (Ca); <0.002% sulfur (S); <0.007% phosphorus (P). Percentage of composition by weight is indicated in Table 1 in the columns corresponding to carbon (C), nickel (Ni), molybdenum (Mo), and vanadium (V).

TABLE 1

Nominal Chemical Composition and Test Samples

| Steel Heat | C | Ni | Mo | V | Ballistic Test Plates (0.250" × 8" × 12") | Tensile Sample | Charpy Impact |
|---|---|---|---|---|---|---|---|
| A: A031 (400 lb VIM) | 0.07 | 10.3 | 1.1 | 0.03 | 12 (9*) | 18 | 27 |
| B: H007 (400 lb VIM) | 0.09 | 9.9 | 1.2 | 0.08 | 9 (9*) | 18 | 27 |
| C: EAF (40 ton EAF) | 0.11 | 10.1 | 1.1 | 0.07 | 8 (3*) | 6 | 9 |
| D: 162 (100 lb VIM) | 0.12 | 9.9 | 1.0 | 0.08 | 9 (9*) | 18 | 27 |
| 163 (100 lb VIM) | 0.12 | 9.9 | 1.0 | 0.08 | 9 (0*) | 0 | 0 |
| E: H009 (400 lb VIM) | 0.15 | 9.9 | 1.2 | 0.08 | 12 (9*) | 18 | 27 |

Uniquely designed heat cycles were employed to determine four key parameters of optimal QLT process, viz., $T_L$ range, $T_T$ range, $t_L$, and $t_T$. The $T_L$ range is the temperature range for an effective martensite to austenite reversion at L-process. The $T_T$ range is the temperature range for the T-process. The $t_L$ is the sufficient holding time for the L-process. The $t_T$ is the holding time for the T-process. The best parameters would generate an optimal microstructure consisting of fine and dense austenite precipitates in a ductile, yet strong, ferrite matrix.

In testing conducted by the present inventor with respect to one-quarter-inch-thick steel plates, the quenching process was characterized by a 40° C. temperature span (between 780° C. and 820° C.) and a 60 minute holding time. The lamellarizing process was characterized by a 30° C. temperature span (between 635° C. and 665° C., or between 635° C. and 665° C.) and a 60 minute holding time. The tempering process was characterized by a 30° C. temperature span (between 575° C. and 605° C.) and a 60 minute holding time. As guidelines for inventive practice, these temperature spans and holding times are especially applicable for inventive steel plates thinner than one inch.

Generally speaking, it is understood by those skilled in the art that the thickness of a steel plate is a factor to be taken into consideration in selecting holding times pertaining to heat treatment of the steel plate. The skilled artisan who reads the instant disclosure will appreciate that, in practicing the present invention, the thickness of an inventive steel plate is to be duly considered in selecting holding times pertaining to each inventive phase of heat processing, viz., the quenching, the lamellarizing, and the tempering.

Dilatometric measurements of more than 20 specimens, coupled with metallographic observations, led to a simple and effective optimal QLT process matrix that includes (i) a 30° C. span for both the L-temperature and the T-temperature, and (ii) a 30 minute holding time for L-process and 60 minutes for T-process.

Details of this matrix for the five 10Ni steel heats are summarized in Table 2, below. There are nine QLT processes of different L and T combinations for heats A031, H007, #162, and H009, and only three QLT processes for heat EAF. These thirty-nine different QLT processes were used to heat treat the thirty-nine machined ballistic plates (0.25"×8"×12") of the five 10Ni steel heats.

TABLE 2

Optimal QLT Process Matrix for Five 10Ni Steel Heats

| Heat | L-temperature ° C. | L-time min | T-temperature ° C. | T-time min | Number of L and T combinations |
|---|---|---|---|---|---|
| A: A031 | 635, 650, 665 | 30 | 575, 590, 605 | 60 | 9 |
| B: H007 | 635, 650, 665 | 30 | 575, 590, 605 | 60 | 9 |
| C: EAF | 650 | 30 | 575, 590, 605 | 60 | 3 |
| D: #162 | 635, 650, 665 | 30 | 575, 590, 605 | 60 | 9 |
| E: H009 | 625, 640, 655 | 30 | 575, 590, 605 | 60 | 9 |

The thirty-nine ballistic test plates from 5 10Ni steel heats were QLT-treated at a company location and were tested at the Army Aberdeen Test Center for their .30 cal. FSP ballistic resistances. Previous 20 mm FSP ballistic test results of four 0.09C-10Ni steel plates (H007 and H008) were extraordinary, as indicated in FIGS. 4 through 7.

In this study, ballistic test plate B5 of heat H007 was heat treated with the same QLT process as that of the previous four samples. Therefore, sample B5 is assumed to possess the same superior properties as that of the four previous 0.09C-10Ni steel samples. Hence, the caliber .30 FSP ballistic limit of sample B5 is assumed to be representative of the superior $V_{50}$ and is designated as $V_{50R}$ in this study.

Figure 8:
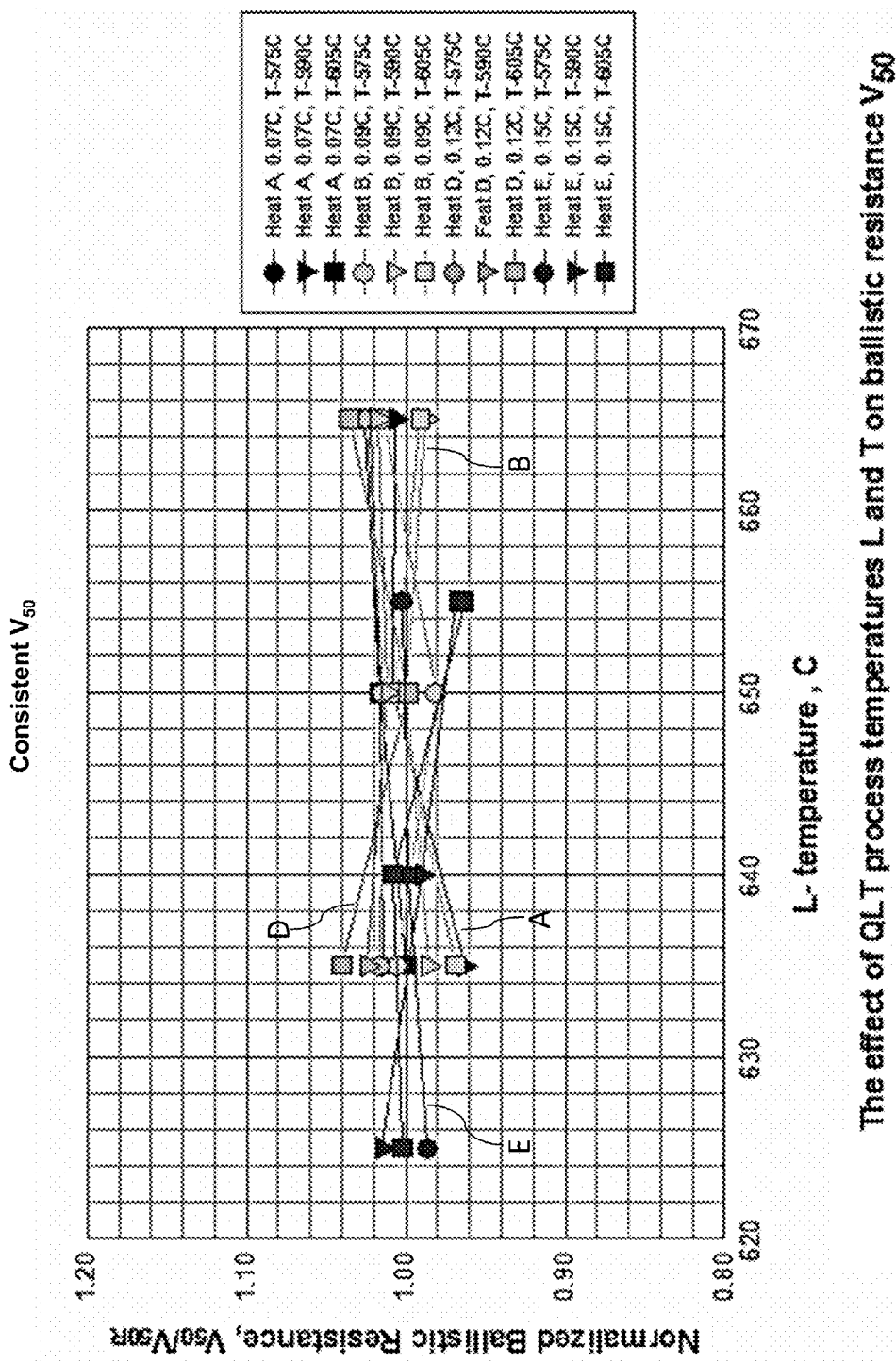
FIG. 8 is a graph illustrating normalized ballistic resistance versus tensile strength for four 10Ni steel test heats, viz., heats A, B, D, and E, in accordance with the present invention.
Figure 9:
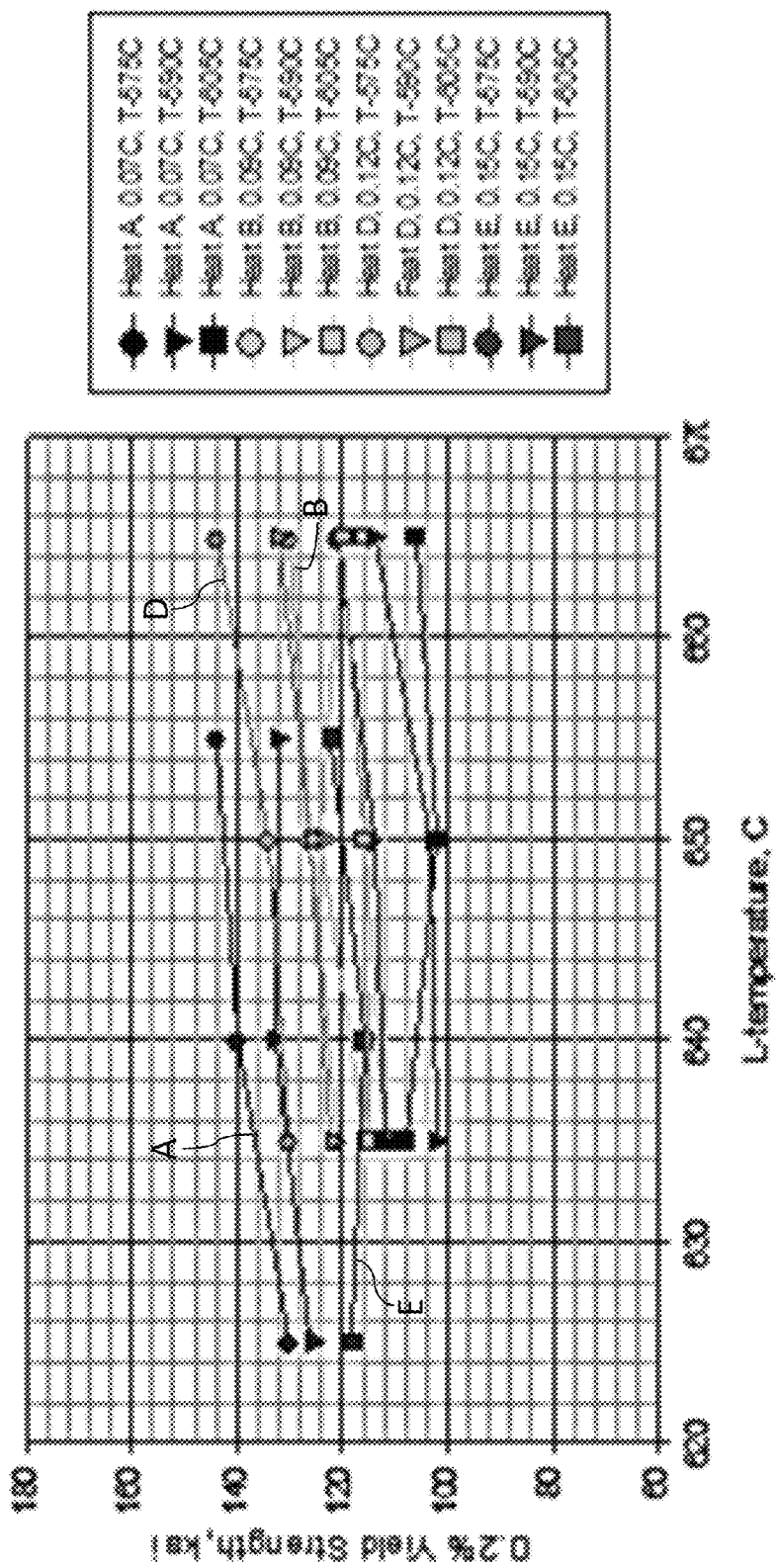
FIGS. 9 through 12 are graphs illustrating the effects of QLT processing on the mechanical properties of the four 10Ni steel heats to which FIG. 8 pertains. In particular, with respect to each 10Ni steel heat, variation in accordance with process temperature L is shown for yield strength (FIG. 9), tensile strength (FIG. 10), Charpy V-notch impact-testing number (FIG. 11), and elongation (FIG. 12).
Figure 10:
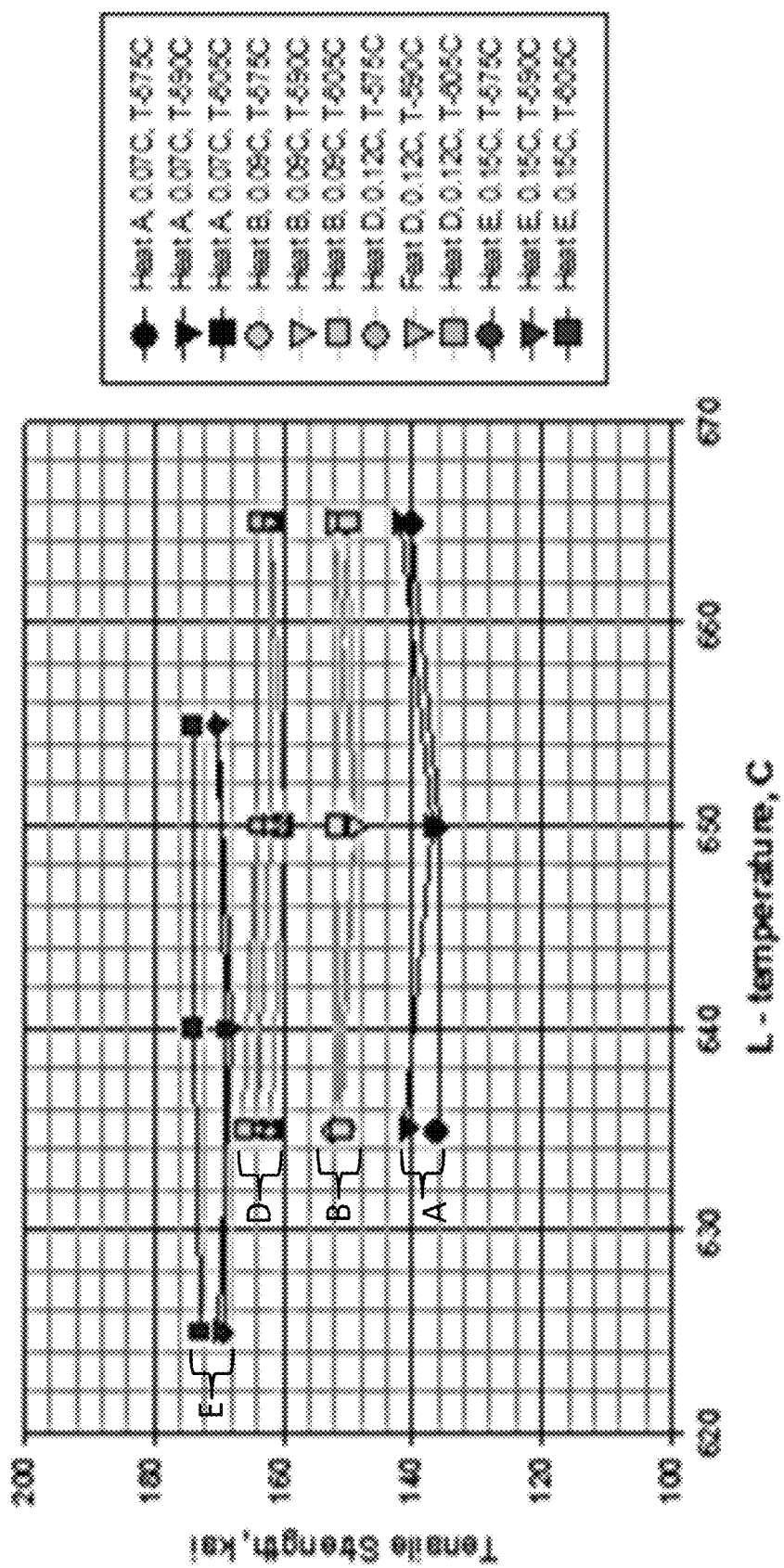
Figure 11:
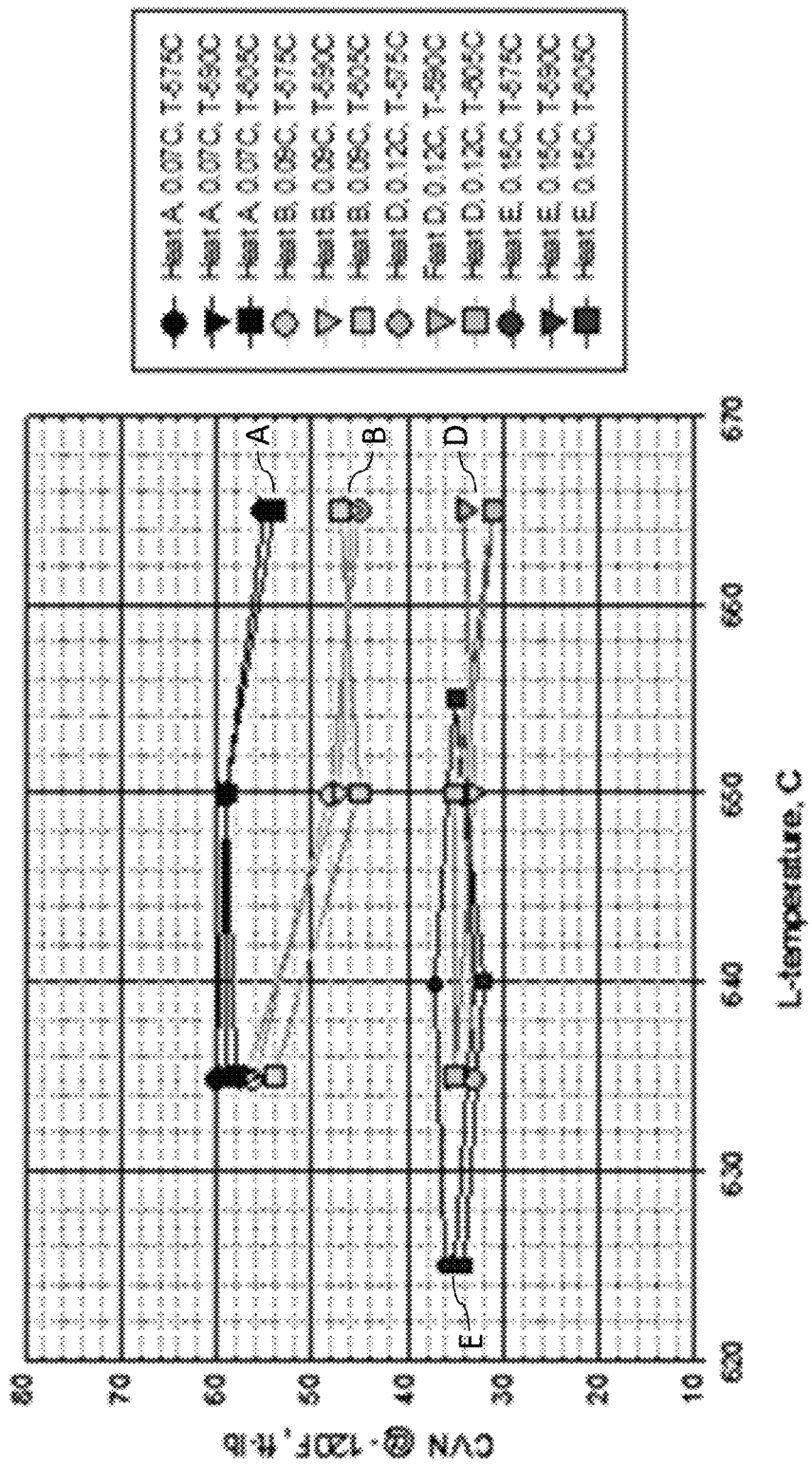
Figure 12:
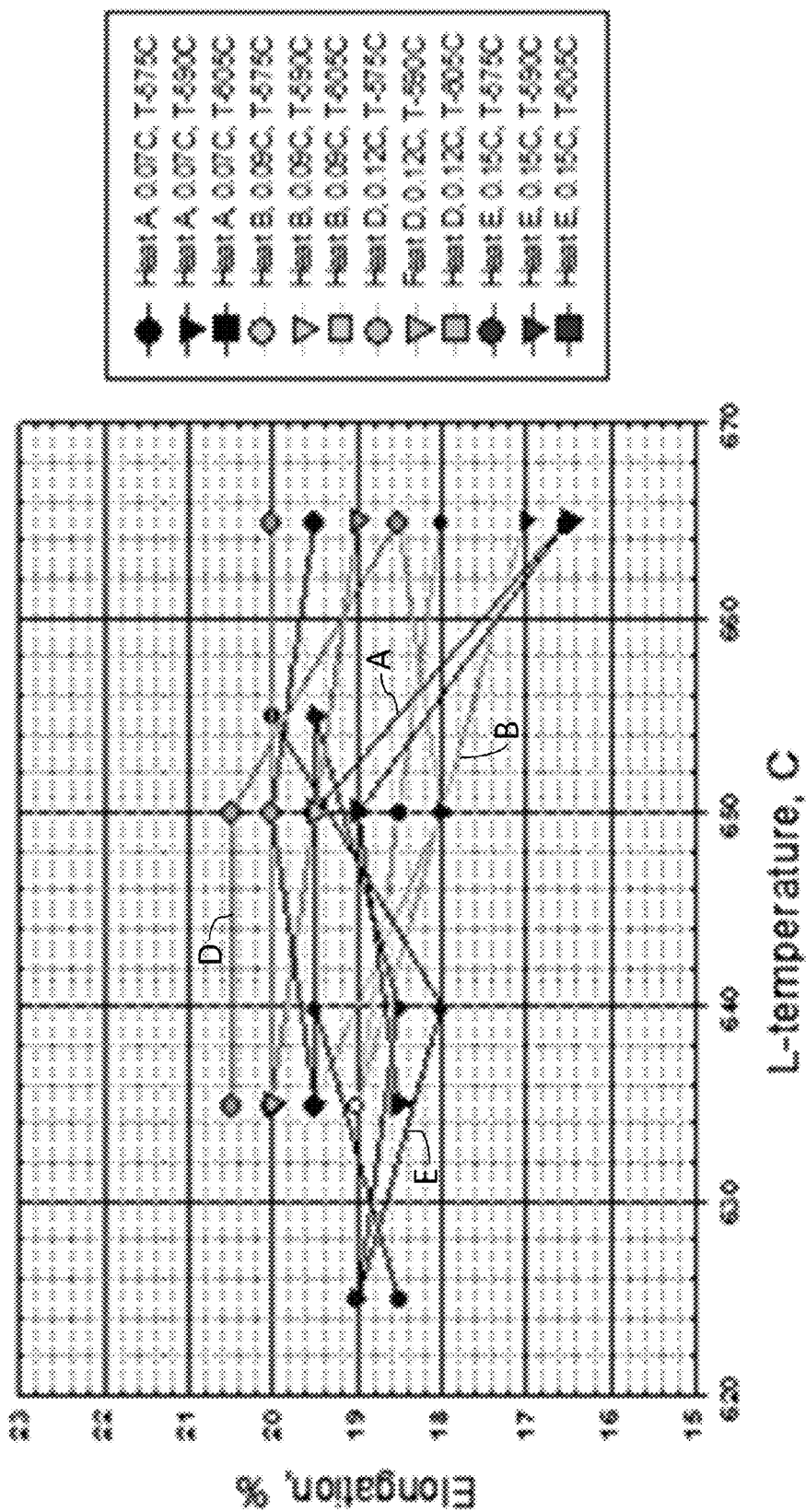

As illustrated in FIG. 8, normalized ballistic resistance $V_{50}/V_{50R}$ was plotted against temperatures L and T with fixed holding times. FIG. 8 demonstrates the effect of QLT process temperatures L and T on ballistic resistance $V_{50}$. The thirty-nine normalized $V_{50}/V_{50R}$ values fall within a narrow band between 0.96 and 1.04 over the entire optimal QLT process test matrix, and thus show no more than 4% deviation from the reference ballistic resistance $V_{50R}$. This is an acceptable range from commercial production and naval application standpoints.

In conclusion, the steel manufactured with (i) carbon content range between 0.07% and 0.15%, (ii) QLT process test matrix with a 30° C. span in both the L-temperature and the T-temperature, and (iii) holding times of 30 minutes for L-process and 60 minutes for T-process, exhibits superior ballistic properties as previously observed by the present inventor in optimal QLT-treated 0.09C-10Ni steel plates.

Notable are the mechanical properties of the thirty-nine tested ballistic plates. Two 0.25-inch (6.35 mm) flat tensile specimens and three half-width V-notch Charpy impact specimens were machined from each of the tested ballistic plates of five 10Ni steel heats. The tensile tests were performed at room temperature and Charpy impact tests at −120° F.

Results are illustrated in FIGS. 9 through 12, which demonstrate the effect of QLT process on the mechanical properties of four of the five 10Ni steel heats. Note that the data of heat C were obscured by other data and hence are omitted in FIGS. 9 through 12.

It should be pointed out that the two surfaces of the tensile specimen are in an un-machined, hot-rolled, and heat-treated condition that causes a rough surface finishing and a decarburization layer of up to 0.015 inch (0.6 mm) deep. This poor surface condition is detrimental to the strength and ductility of the steel. However, it is difficult to quantitatively estimate the magnitude of this effect on each sample, and FIGS. 9 through 12 were plotted without any correction for this poor surface condition.

Although ballistic resistance $V_{50}$ of the QLT processed 10Ni steel plates was insensitive to carbon content, tensile strength and impact toughness were affected considerably by it. Heat H009, with the highest carbon content at 0.15%, displayed the highest strength and lowest impact toughness. Heat A031, having the lowest carbon content, displayed the lowest strength and highest impact toughness. This unique deviation between ballistic behavior and mechanical properties is well illustrated in FIG. 13, and makes possible a class of 10 Ni steel that possesses a range of strength and toughness but maintains a common superior ballistic resistance $V_{50}$.

Figure 13:
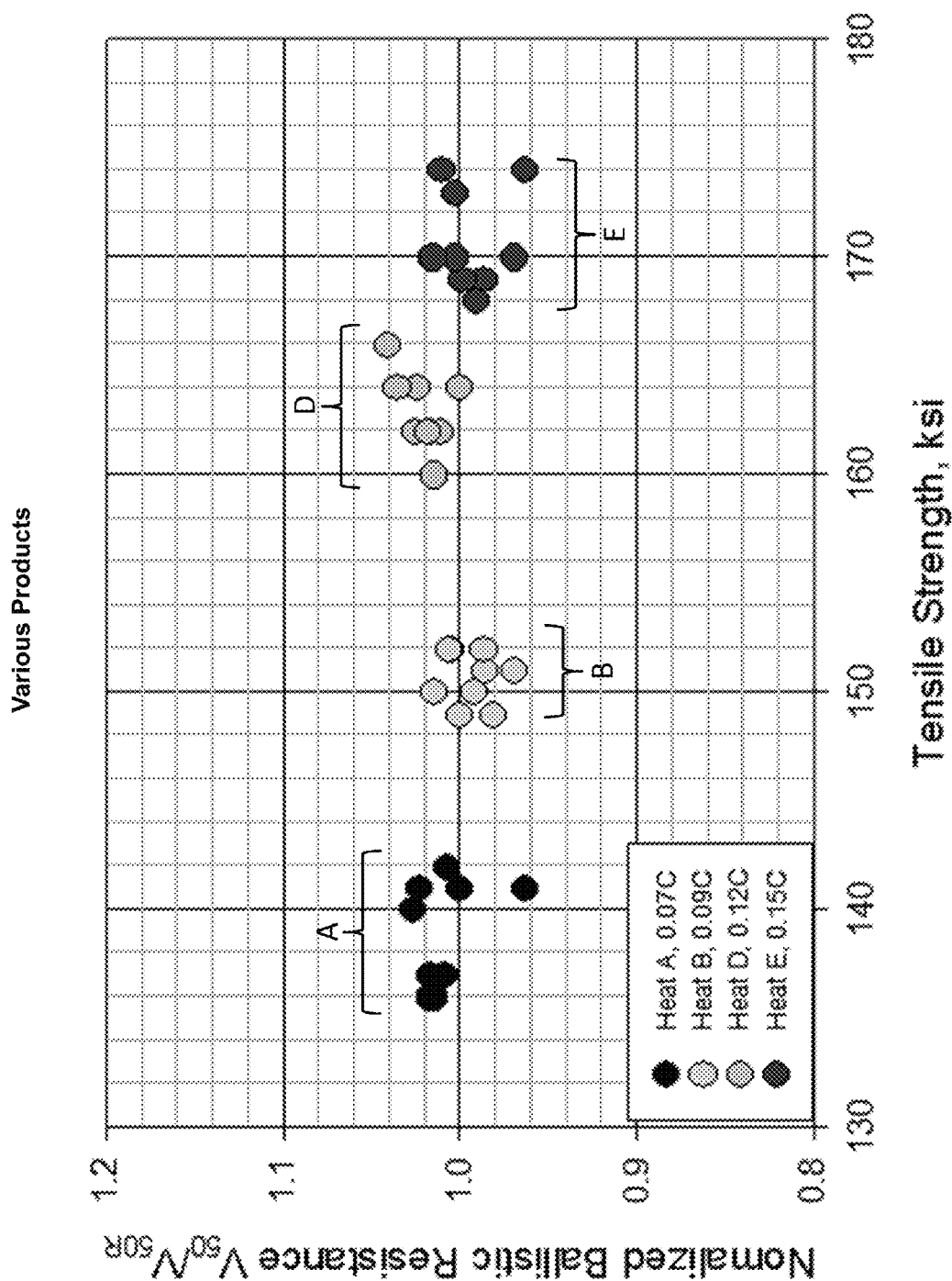
FIG. 13 is a graph illustrating normalized ballistic resistance versus tensile strength for the four steel heats to which FIGS. 8 through 12 pertain.

FIG. 13 is a graph illustrating deviation between ballistic resistance V50 and tensile strength of four QLT 10Ni steel heats. Note that the QLT processed H007 samples showed only slightly lower strength and ductility, and comparable impact toughness, relative to the previous FY11 tests (FIGS. 4 through 7), confirming that these two study results are consistent.

Particularly noteworthy with regard to microstructure characterization, FIGS. 14 through 17 are photographic renditions of ballistic plate A5. These figures show Ni-rich austenite precipitates. Metallography, electron backscatter diffraction (EBSD), and energy dispersive X-ray spectrometry (EDS) performed on a large number of tested ballistic plates confirmed that all samples displayed a common desirable microstructure feature—viz., fine and dense austenite precipitates in a ferrite matrix, such as illustrated by FIG. 14. EDS maps such as portrayed in FIGS. 15 through 17 confirmed that the nearly spherical particles are nickel-rich austenite precipitates. EBSD results could only reveal a few large austenite particles because a severe edge effect interfered with orientation diffraction patterns of small particles.

The test results and characteristics and the microstructure observations in this study further confirmed the present inventor's BIP theory and, more specifically, the key microstructure components that result in superior overall properties of the inventive QLT 10Ni steel. Additional testing, such as involving greater improvements in sample preparation, may provide even further confirmation.

Table 3, below, shows a comparison between the mechanical property requirements in ASTM specification A553 for cryogenic application, and the properties of the present invention's QLT 10 Ni steel. The inventive steel far exceeds the current cryogenic steel SA553 requirements.

TABLE 3

Mechanical Property Comparison between 10Ni Steel and ASTM A553 Requirements

| Steel | Heat | Tensile Property (Room Temperature) | | | CVN (TL)@-320° F. ft-lb |
|---|---|---|---|---|---|
| | | YS, ksi | TS, ksi | Elongation, % | |
| A553 | QT or QLT | 85 | 100-120 | 20 | ≥20 (TL) |
| 10 Ni (H007) | QLT | 130 | 158 | 23 | 42 |

The present inventor is exploring other potential applications (e.g., commercial applications) of his QLT 10Ni steel. There may be interest in adapting the inventive 10Ni steel to create a new, ultra-high-strength plate steel for energy-related commercial cryogenic applications. Efforts are underway for the Navy to form a joint research team with a company. The present inventor believes that he can make further determinations with respect to commercially acceptable chemical compositions and QLT process ranges, thus facilitating technology transfer of his inventive steel.

As previously discussed herein, the superior ballistic resistance of previous tests (FY11) of optimal QLT treated H007 samples can be consistently reproduced in thirty-nine samples of five 10Ni steel heats with a carbon content range between 0.07% and 0.15%. These composition and QLT process ranges are achievable in commercial steel production. The inventive steel is superior to current naval steel HSLA 115, and could further improve the performance and survivability of the naval fleet. Moreover, the novel technology of the present invention appears to be commercial production-ready, i.e., ready to be tech-transferred for commercial production.

The inventive steel's stability in ballistic resistance (fluctuation<4%) over a moderate variation in strength and toughness can provide a range of combinations of mechanical property and ballistic performance for various applications. The mechanical properties (e.g., strength and toughness) of the inventive steel are mainly a function of carbon content.

The present invention, which is disclosed herein, is not to be limited by the embodiments described or illustrated herein, which are given by way of example and not of limitation. Other embodiments of the present invention will be apparent to those skilled in the art from a consideration of the instant disclosure, or from practice of the present invention. Various omissions, modifications, and changes to the principles disclosed herein may be made by one skilled in the art without departing from the true scope and spirit of the present invention, which is indicated by the following claims.

What is claimed is:

1. A method for making a steel article, the method comprising:
   forming an iron alloy that includes, prior to heat treatment: carbon constituting a weight percent in the range of 0.07 to 0.15; nickel constituting a weight percent in the range of 9 to 11; molybdenum constituting a weight percent in the range of 0.8 to 1.2; vanadium constituting a weight percent in the range of 0.05 to 0.1; additive or impurity elements including manganese and chromium, said manganese constituting a weight percent in the range of 0.5 to 0.7, said chromium constituting a weight percent in the range of 0.5 to 0.7; with a balance of said iron alloy being iron;
   heat treating said iron alloy, wherein said heat treating includes:
   quenching said iron alloy in accordance with a temperature span of 780 degrees Celsius to 820 degrees Celsius, and a 60 minute holding time;
   lamellarizing the quenched said iron alloy in accordance with a thirty degrees Celsius temperature span of 625-635 degrees Celsius to 655-665 degrees Celsius, and a 30 minute holding time;
   tempering the quenched and lamellarized said iron alloy in accordance with a temperature span of 575 degrees Celsius to 605 degrees Celsius, and a 60 minute holding time.

2. The method of claim 1, wherein said iron alloy essentially consists of, prior to said heat treatment: said carbon; said nickel; said molybdenum; said vanadium; said manganese; said chromium; silicon constituting a weight percent in the range of 0.15 to 0.25; copper constituting a weight percent in the range of 0.1 to 0.2; niobium constituting a weight percent in the range of 0.001 to 0.010; aluminum constituting a weight percent in the range of 0.02 to 0.05; titanium constituting a weight percent in the range of 0.001 to 0.010; calcium constituting a weight percent in the range of 0.001 to 0.005; nitrogen constituting a weight percent of not more than 0.009 weight percent nitrogen; oxygen constituting a weight percent of not more than 0.003; phosphorus constituting a weight percent of not more than 0.009; sulfur constituting a weight percent of not more than 0.004.

3. An article comprising a steel composition made by the method including forming an iron alloy and performing heat treatment of the alloy, wherein:
the performing of the heat treatment includes quenching the alloy, lamellarizing the quenched alloy, and tempering the quenched, lamellarized alloy;
prior to the performing of the heat treatment, the alloy includes, by weight, 0.07 to 0.15% C, 9 to 11% Ni, 0.8 to 1.2% Mo, 0.05 to 0.10% V, and further includes additives and/or impurities including, by weight, 0.5 to 0.7% Mn and 0.5 to 0.7% Cr, with a balance being Fe;
the lamellarizing of the quenched alloy is performed in accordance with a 30 minute holding time and a thirty degrees Celsius temperature span in the range between 625° C. and 665° C.
the tempering of the quenched, lamellarized alloy is performed in accordance with a 60 minute holding time and a temperature span of 575° C. to 605° C.

4. The article of claim 3, wherein the article is a steel plate.

5. The article of claim 3, wherein the additives and/or impurities further include at least one of the following: 0.15 to 0.25% Si; 0.1 to 0.2% Cu; 0.001 to 0.010% Nb; 0.02 to 0.05% Al; 0.001 to 0.010% Ti; 0.001 to 0.005% Ca; not more than 0.009% N; not more than 0.003% O; not more than 0.009% P; not more than 0.004% S.

6. The article of claim 5, wherein the steel composition has at least one of the following properties:
yield strength of at least 129 ksi;
tensile strength of at least 157 ksi;
elongation of at least 23%;
Charpy impact energy of at least 112 foot-pounds at −120° F.

7. The article of claim 6, wherein the article is a steel plate.

8. The article of claim 3, wherein the additives and/or impurities further include 0.15 to 0.25% Si.

9. The article of claim 3, wherein the additives and/or impurities further include 0.1 to 0.2% Cu.

10. The article of claim 3, wherein the additives and/or impurities further include 0.15 to 0.25% Si and 0.1 to 0.2% Cu.

11. The method of claim 1, wherein the heat treated said iron alloy is characterized by a 20 mm FSP ballistic limit $V_{50}$ that is at least 13% higher than the 20 mm FSP ballistic limit $V_{50}$ of HSLA-100.

12. The article of claim 5, wherein the steel composition has a 20 mm FSP ballistic limit $V_{50}$ that is at least 13% higher than the 20 mm FSP ballistic limit $V_{50}$ of HSLA-100.

* * * * *